United States Patent
Long et al.

(10) Patent No.: US 12,277,704 B2
(45) Date of Patent: Apr. 15, 2025

(54) METHODS AND SYSTEMS FOR PREDICTING COMPLICATIONS POST-ENDOVASCULAR ANEURYSM REPAIR

(71) Applicants: Yanyu Long, Saginaw, MI (US); John Blebea, Saginaw, MI (US)

(72) Inventors: Yanyu Long, Saginaw, MI (US); John Blebea, Saginaw, MI (US)

( * ) Notice: Subject to any disclaimer, the term of this patent is extended or adjusted under 35 U.S.C. 154(b) by 391 days.

(21) Appl. No.: 17/841,666

(22) Filed: Jun. 16, 2022

(65) Prior Publication Data
US 2024/0331135 A1    Oct. 3, 2024

(51) Int. Cl.
| | |
|---|---|
| G06T 7/00 | (2017.01) |
| A61B 6/03 | (2006.01) |
| A61B 6/50 | (2024.01) |
| G06T 3/40 | (2006.01) |
| G16H 30/40 | (2018.01) |
| G16H 50/20 | (2018.01) |

(52) U.S. Cl.
CPC ............ *G06T 7/0012* (2013.01); *A61B 6/032* (2013.01); *A61B 6/504* (2013.01); *G06T 3/40* (2013.01); *G16H 30/40* (2018.01); *G16H 50/20* (2018.01); *G06T 2200/04* (2013.01); *G06T 2207/10081* (2013.01); *G06T 2207/20081* (2013.01); *G06T 2207/20084* (2013.01); *G06T 2207/30101* (2013.01)

(58) Field of Classification Search
None
See application file for complete search history.

(56) References Cited

U.S. PATENT DOCUMENTS

2021/0153808 A1*   5/2021   Tada ..................... G06T 7/0016

OTHER PUBLICATIONS

Kordzadeh et al., Prediction, pattern recognition and modelling of complications post-endovascular infra renal aneurysm repair by artificial intelligence, Vascular, vol. 29(2), 2021, pp. 171-182.

* cited by examiner

*Primary Examiner* — Lennin R Rodriguezgonzalez

(57) ABSTRACT

Methods and systems for predicting post-operative complications after EVAR, including calculating a post-operative complication probability of a patient after EVAR, which comprises generating a plurality of 3D CTA reconstruction images of the patient with abdominal aortic aneurysm; and providing the plurality of 3D CTA reconstruction images of the patient to a prediction neural network configured to predict post-operative complications after endovascular aneurysm repair. The prediction neural network is trained by generating one or more datasets including a plurality of post-operative 3D CTA reconstruction images of patients after EVAR; selecting a first set of images showing positive post-operative complications and a second set of images showing negative post-operative complications in accordance with a determined positive:negative ratio; determining a training input by downsampling the second set of images and augmenting the first set of images and the downsampled second set of images; and providing the training input to the prediction neural network.

20 Claims, 5 Drawing Sheets

METHODS AND SYSTEMS FOR PREDICTING COMPLICATIONS POST-ENDOVASCULAR ANEURYSM REPAIR

FIELD

The present disclosure relates to methods and systems for predicting complications after endovascular aneurysm repair (EVAR).

BACKGROUND

Predicting complications following abdominal endovascular aneurysm repair (EVAR) is an important clinical and research topic in vascular surgery. Endoleak, graft migration, and rupture following EVAR culminate in a higher rate of re-intervention than is seen after open abdominal aortic aneurysm (AAA) repair. Even though life-threatening complications after EVAR are rare, the occurrence of complications is associated with increased morbidity, high medical cost, and potential mortality. Therefore, regular surveillance imaging is necessary to detect these complications after EVAR. However, regular surveillance with Computer Tomography (CT) scanning is associated with additional radiation exposure, which may increase cancer-related mortality, such as was seen in the EVAR-1 and DREAM trails. Identifying high-risk patients who should undergo more frequent surveillance and low-risk patients who require less would help to improve patient compliance and clinical outcomes.

Artificial Intelligence (AI) has revolutionized many areas of research with possible applications in health care in the near future. Several studies have reported the use of AI techniques to predict EVAR complications, but the results were not promising. This appears to reflect the difficulties of applying AI algorithms to vascular surgery databases, which are by nature imbalanced (complication rates are low) and with skewed data distribution.

DETAILED DESCRIPTION

Figure 1:
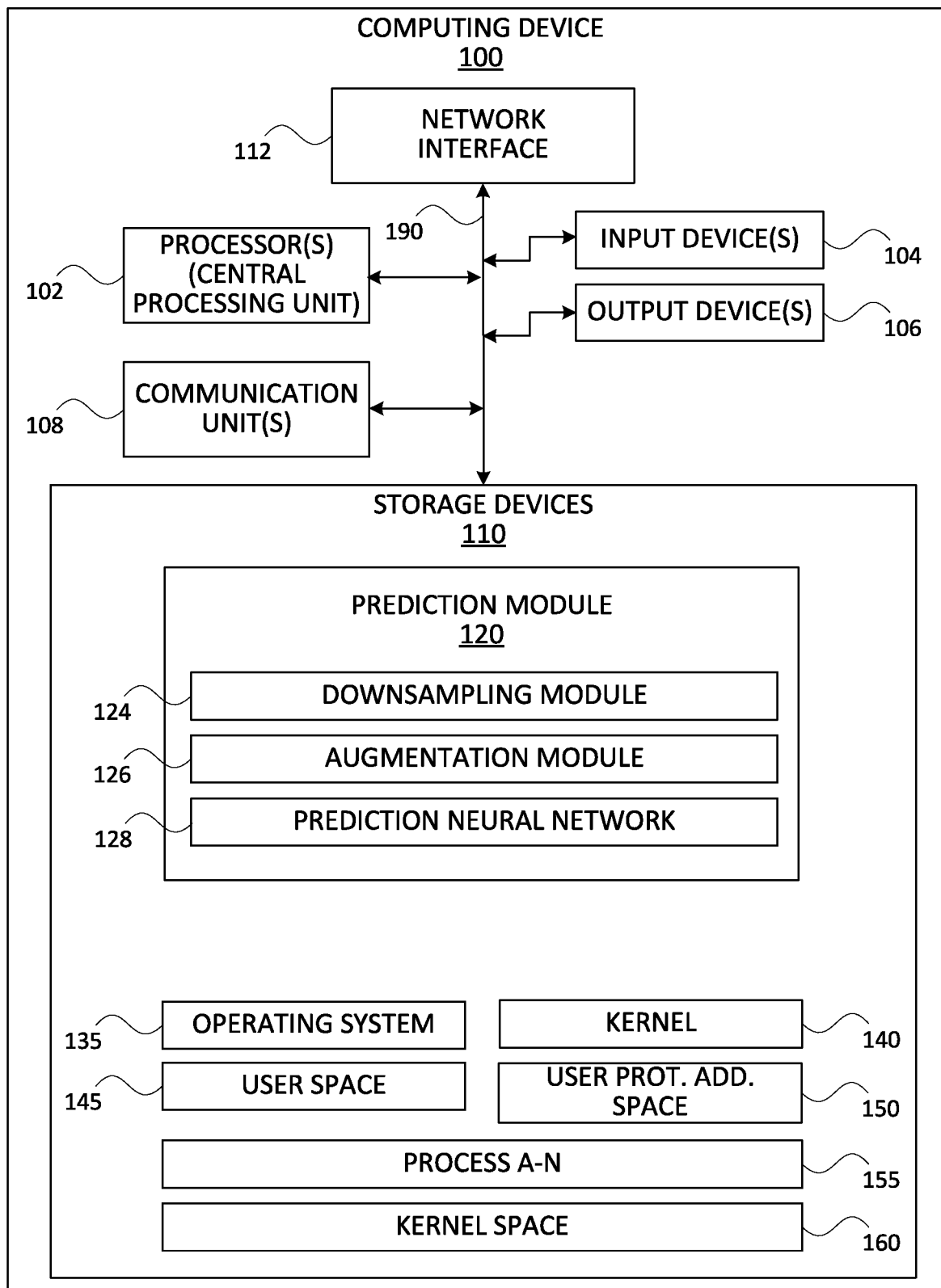
FIG. 1 is a functional block diagram illustrating an example computing device that is configured to use a neural network to predict post-operative complications after endovascular aneurysm repair, incorporated with teachings of the present disclosure, according to some embodiments.

In addition to other locations, defined terms may be found at the end of this Detailed Description.

In overview, this disclosure relates to systems and methods performed by and in a computing apparatus to predict post-operative complications following endovascular aneurysm repair (EVAR) and evaluate the risks of potential surgery for a patient having an abdominal aortic aneurysm. The systems may include one or more computing devices. The methods are performed by one or more computing devices.

The current disclosure provides a novel prediction model with high accuracy for clinical priority. A novel convolutional neural network model is used, which can automatically extract data with minimal human annotation. Training data for the convolutional neural network model comes from raw 3-dimensional reconstruction images of patients who have undergone EVAR, which are downsampled and augmented to enlarge the size of the original dataset and balance the skewed distribution in order to better capture infrequent complications in the data. The output of the network is the probability that a patient would have post-operative complications after EVAR.

This pure data-driven approach, with minimal human annotation, can be helpful in solving an important problem in vascular surgery. Previous artificial intelligent models tend to focus on improving the overall accuracy but neglect to recognize that positive cases are of much higher clinical priority. For example, Kordzadeh A, Hanif M A, Ramirez M J, Railton N, Prionidis I, Browne T. Prediction, pattern recognition and modeling of complications post-endovascular infrarenal aneurysm repair by artificial intelligence. *Vascular.* 2021; 29(2):171-182 has reported the accuracy of their EVAR complication model to be greater than 86%. However, in the analysis of type I endoleaks, the model predicts all the cases to be negative, while for type III endoleaks, 30 out of 32 are predicted negative (both predicted positive cases were incorrect). A closer look at the results indicated that their model tends to predict most cases as negative, which consists of the low overall incidence of endoleaks. However, in clinical practice, it is desired to identify the high-risk patients to avoid missing life-threatening complications instead of pursuing a high overall accuracy. In other words, enhancing the sensitivity of the model to find all positive cases should be of higher priority.

The training data may be modified by downsampling to correct a data imbalance issue (see detailed discussion below). Data imbalance is the likely contributing factor responsible for the low sensitivity of prior models. More specifically, according to an example embodiment of the present disclosure, a total complication rate is calculated as 17.6%(48 out of 273). With such a low complication rate, predicting most cases as negative induces data-driven artificial intelligent models to maximize accuracy.

While downsampling can alleviate the imbalance issue, it would also negatively impact the overall model accuracy due to the loss of data. To compensate for this, the downsampled data is augmented, and thus, the dataset size is enlarged. In an example embodiment, after applying the data downsampling and augmentation techniques, the sensitivity of the prediction model has increased to 100% with a specificity of 44%. This results in successfully identifying all the complications, although at the cost of 20/28=71% false positives. These patients would continue to undergo expected clinical surveillance. However, the negative predictive value of 100% is excellent and means that all the predicted negative cases are correct. The current prediction model therefore successfully identifies the low-risk group of patients who are not at risk of complications and therefore can safely undergo less frequent surveillance.

Compared to existing methods, the current disclosure does not require any expert-annotated data but only the abdominal aortic aneurysm (AAA) computed tomography angiography (CTA) images as input. The current disclosure may also be applicable to the broader medical research community using clinical datasets that are relatively small and skewed in outcome distributions. The current disclosure, either alone or combined with other prediction models, may be used more broadly in other areas of peripheral arterial and carotid artery disease.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made without departing from the spirit or scope of the subject matter presented here.

FIG. 1 is a functional block diagram illustrating an example computing device 100 that is configured to use a prediction neural network 128 to predict post-operative complications after endovascular aneurysm repair, incorporated with teachings of the present disclosure, according to some embodiments. FIG. 1 illustrates only one particular example of computing device 100, and many other examples of computing device 100 may be used in other instances and may include a subset of the components included in the example computing device 100. Computing device 100 may include additional components not shown in FIG. 1.

As shown in the example of FIG. 1, computing device 100 includes one or more processors (Central Processing Unit) 102, one or more input devices 104, one or more output devices 106, one or more communication units 108, one or more storage devices 110, and network interface 112. Processors 102, input devices 104, output devices 106, communication units 108, storage devices 110, and network interface 112 are interconnected via bus 190. Storage devices 110 include prediction module 120. Prediction module 120 may include downsampling module 124, augmentation module 126, and prediction neural network 128.

Processor 102 may include one or more execution cores (CPUs). For example, computing device 100 may also include a peripheral controller hub (PCH) (not shown). In another example, computing device 100 may also include a sensors hub (not shown). Input devices 104 and output devices 106 may include, for example, user interface device(s) including a display, a touch-screen display, printer, keypad, keyboard, etc., sensor(s) including accelerometer, global positioning system (GPS), gyroscope, etc., communication logic, wired and/or wireless, storage device(s) including hard disk drives, solid-state drives, removable storage media, etc. I/O ports for input devices 104 and output devices 106 may be configured to transmit and/or receive commands and/or data according to one or more communications protocols. For example, one or more of the I/O ports may comply and/or be compatible with a universal serial bus (USB) protocol, peripheral component interconnect (PCI) protocol (e.g., PCI express (PCIe)), or the like.

Processors 102 may implement functionality and/or execute instructions within computing device 100. For example, processors 102 on computing device 100 may receive and execute instructions stored by storage devices 110 that provide the functionality of prediction module 120. These instructions executed by processors 102 may cause computing device 100 to store and/or modify information within storage devices 48 during program execution.

Storage devices 110 may generally comprise a random access memory ("RAM"), a read-only memory ("ROM"), and a permanent mass storage device, such as a disk drive or SDRAM (synchronous dynamic random-access memory). Computing device 100 may store program code for modules and/or software routines.

Storage devices 110 may also store operating system 135. Storage devices 110 may also include kernel 140, kernel space 160, user space 145, and user protected address space 150. Storage devices 110 may store one or more processes 155 (i.e., executing software application(s)). Process 155 may be stored in user space 145. Process 155 may include one or more other processes 155a . . . 155n. One or more process 155 may generally execute in parallel, i.e., as a plurality of processes and/or a plurality of threads. In some embodiments, operating system 135 may include kernel 140. Operating system 135 and/or kernel 140 may attempt to protect kernel space 160 and prevent access by certain of processes 155a . . . 155n. These software components may be loaded from a non-transient computer-readable storage medium into computing device storage devices 110 using a drive mechanism associated with a non-transient computer-readable storage medium, such as a floppy disc, tape, DVD/CD-ROM drive, memory card, or other like a storage medium. In some embodiments, software components may also or instead be loaded via a mechanism other than a drive mechanism and computer-readable storage medium (e.g., via network interface 112).

Kernel 140 may be configured to provide an interface between user processes and circuitry associated with computing device 100. In other words, kernel 140 may be configured to manage access to processor 102, I/O ports and peripheral devices by process 155. Kernel 140 may include one or more drivers configured to manage and/or communicate with elements of computing device 100.

Figure 2:
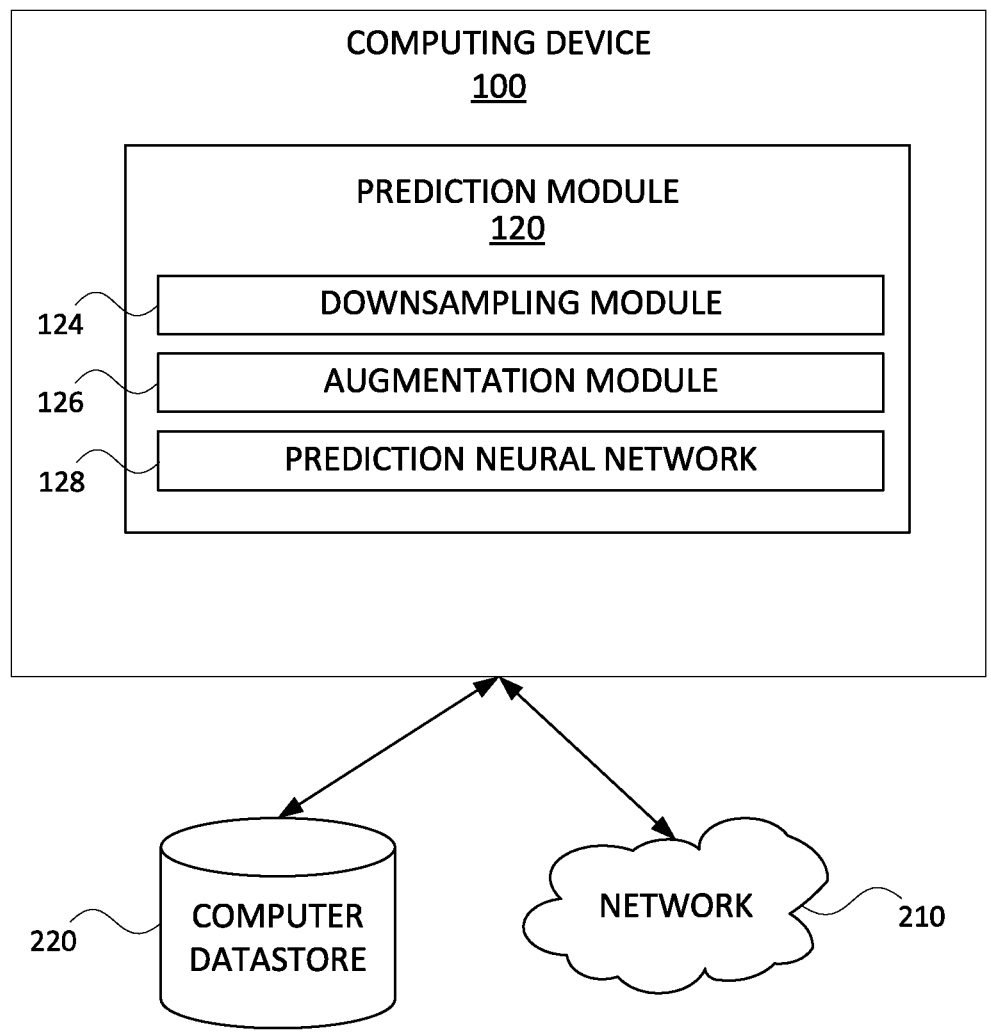
FIG. 2 is a network and device diagram illustrating an example computing device of FIG. 1 and a network incorporated with teachings of the present disclosure, according to some embodiments.

FIG. 2 is a network and device diagram illustrating computing device 100 of FIG. 1, network 210 and computer datastore 220, according to some embodiments.

Network 210 may comprise computers, network connections among the computers, and software routines to enable communication between the computers over the network connections. Examples of network 210 comprise an Ethernet network, the Internet, and/or a wireless network, such as a GSM, TDMA, CDMA, EDGE, HSPA, LTE, or other network provided by a wireless service provider. Connection to Network 210 may be via a Wi-Fi connection. More than one network may be involved in a communication session between the illustrated devices. Connection to network 210 may require that the computers execute software routines which enable, for example, the seven layers of the OSI model of computer networking or equivalent in a wireless phone network.

Computing device 100 may also comprise or communicate via bus 190 and/or network interface 110 with computer datastore 220. In various embodiments, bus 190 may comprise a high-speed serial bus, and network interface 110 may be coupled to a storage area network ("SAN"), a high speed wired or wireless network, and/or via other suitable communication technology. Computing device 100 may, in some embodiments, include many more components than illustrated. However, it is not necessary that all components be shown in order to disclose an illustrative embodiment. Computing device 100 may communicate or connect via network 210 to external devices.

Figure 3:
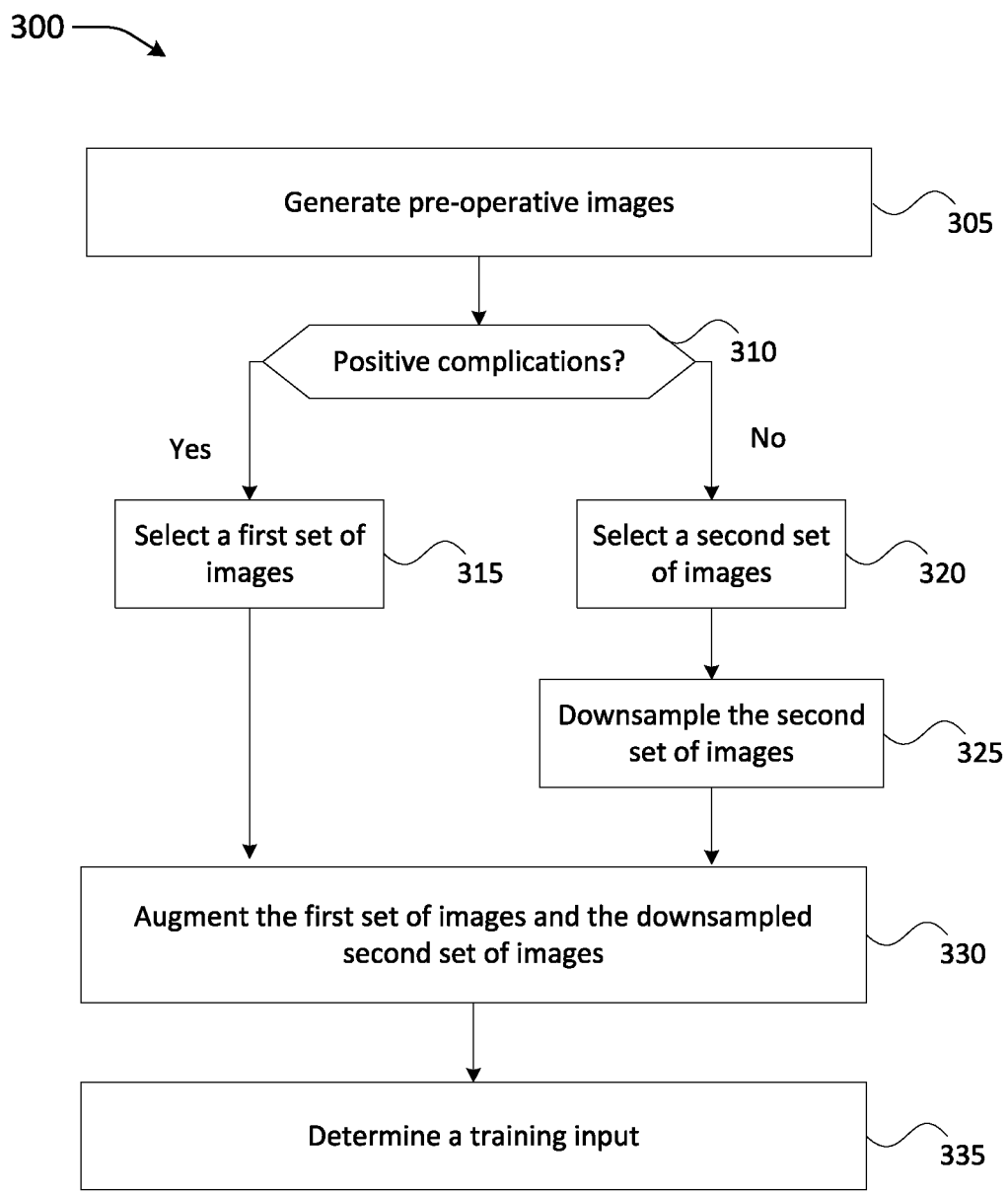
FIG. 3 is a flow diagram illustrating an example of training a prediction neural network, which may be performed by a computing device, according to some embodiments.

FIG. 3 is a flow diagram illustrating an example of training prediction neural network 128, which may be performed by computing device 100 or other computing devices communicating with computing device 100, according to some embodiments. Process 300 will be described as being performed by a system of one or more computing devices located in one or more locations.

At block 305, the system generates 3-dimensional CTA reconstruction images of patients. These images may be a series of 2-dimensional images, or 3-dimensional images of patients after endovascular aneurysm repair. In some embodiments, the series of 2-dimensional images may comprise 13 2-dimensional images. In some embodiments, the 3-dimensional CTA reconstruction images may comprise images of patients after endovascular aneurysm repair. These images may be from a database stored on a non-transitory digital storage media (such as computer datastore 220 of FIG. 2).

The 3D CTA images may include pre-operative, intra-operative, or post-operative CTA scans of the abdomen/pelvis with 3D reconstruction images. In the case where a patient has gone through a certain time of after surgery follow-up, this patient's pre-operative, intra-operation, and post-operative (of the previous surgery) can be used as training examples. For example, training examples may include not only post-operative images, but also pre-operative and intra-operative if an patient has gone through EVAR previously, and this patient has been known having positive or negative complications after the follow-up. The images may come from electronic medical records (EMR) and operative logs, which are used to identify patients who have undergone elective EVAR. EMR may be reviewed for patient demographics, pre-operative and post-operative imaging reports, and office visit notes. Clinical data variables may include initial AAA size, age, gender, comorbidities, smoking status, complications, and reinterventions. Comorbidities may include hypertension (HTN), diabetes mellitus (DM), coronary artery disease (CAD), or renal failure. Renal failure is defined as a glomerular filtration rate (GFR) of less than 15 ml/min. Complications may include any type of endoleak, graft migration, AAA rupture, graft limb occlusion, renal artery occlusion, neck dilation, graft infection, pelvic ischemia, and stent strut/barb fracture. All clinical data may be de-identified. Descriptive statistics of clinical data may be analyzed. In some embodiments, intra-operative images may be used in the training datasets to increase accuracy.

At block 310, the system calls or determines whether the 3-dimensional CTA reconstruction images show positive post-operative complications. The images showing positive post-operative complications may be included in a first set of images at block 315. The images not showing positive post-operative complications (showing negative post-operative complications) may be included in a second set of images at block 320. The selection at blocks 315 and 320 may be in accordance with a determined positive:negative ratio. In an example embodiment, a positive:negative ratio may be set to 1:4.7. In other embodiments, different ratios for training:testing and positive:negative may be used.

At block 325, the system may call or trigger the execution of downsampling module 124 of the prediction module 120 to downsample the second set of images. The negative cases in the second set of images may be randomly dropped according to a ratio of n so that the number of positive and negative cases in the training dataset is roughly the same. In an example embodiment, the downsampling ratio is 1:4.7. In other embodiments, other downsampling ratios may be used. The downsampling ratio relates to the positive:negative ratio in the training dataset.

At block 330, the system may call or trigger the augmentation module 126 of prediction module 120 to enlarge the size of the first and second set of images. In an example embodiment, the images are rotated, flipped, or zoomed in to get three additional variations of the original images. These new images may have the same labels as the original ones. The dataset has been enlarged by three times.

Downsampling and augmentation are to correct a data imbalance issue in the training datasets. As complications are infrequent compared to uneventful cases, negative examples may dominate the sample population. If the prediction model is trained with just the original data, the skewed data distribution would force the model to predict most of the cases to be negative in order to attain a high overall accuracy rate. However, this would be undesirable and not clinically useful because in clinical care, it is more desirable not to miss any positive case at the cost of an increased false-positive rate. More specifically, according to an example embodiment of the present disclosure, the total complication rate is 17.6% (48 out of 273). With such a low complication rate, predicting most cases as negative induces data-driven artificial intelligent models to maximize accuracy. Therefore, downsampling may be applied on the second set of images that shows negative post-operative complications. In the downsampling, only part of the negative cases may be randomly selected from the whole set, such that the positive and negative sets of data have similar numbers.

While downsampling can alleviate the imbalance issue, it might also negatively impact the model accuracy due to the loss of data. To compensate for this, a data augmentation technique may be employed to re-enlarge the dataset size. The augmentation may include at least one of the following operations to the images: rotating, cropping, color jittering, blurring and resizing. After the augmentation, the processed images may look visually similar to the original ones, but they are quite different in terms of representation and are considered new data to the model. The operations to the images may enlarge the dataset four-fold. Since data augmentation is applied simultaneously to both positive and negative cases, it did not reintroduce an imbalance issue.

At block 335, the system determines a training input for the prediction neural network 128 that is configured to predict post-operative complications after endovascular aneurysm repair. The prediction may be represented by a probability of confidence score of the occurrence of post-operative complications after endovascular aneurysm repair. In some embodiments, there may be multiple images for each patient. All images may be entered into prediction neural network 128 to get a probability output for each image and then the probabilities may be averaged to obtain a final probability.

The prediction neural network 128 may be a convolutional neural network. A convolutional neural network is often applied to image processing and enables detection, segmentation, and recognition of objects and regions within images. The prediction neural network 128 may comprise a multilayered network with a mathematical model simulating some of the properties of the visual cortex. The input is the raw images with a resolution of 180×180. In an example embodiment, a multilayer convolutional neural network may be used as the model backbone. The structure of the prediction neural network 128 may be a stack of three convolution-maxpooling layers, followed by a nonlinear layer and then a linear fully connected layer. Neurons process portions of the input image and provide a filtered representation of the original image. The process may be repeated in each layer until the final input.

In some embodiments, additional related predictors may be combined and added to the prediction model, such as automated image measurements or expert measured image features along with clinical demographic characteristics and comorbidities. This additional data will provide more information to the model and thus likely increase accuracy.

In some embodiments, the training input may also incorporate specific endografts and their implanted characteristics and conformability to assist in pre-operative planning. Endograft (endovascular graft) is commonly used in endovascular aneurysm repair. It is a kind of graft that is inserted within the aneurysm through small groin incisions.

Figure 4:
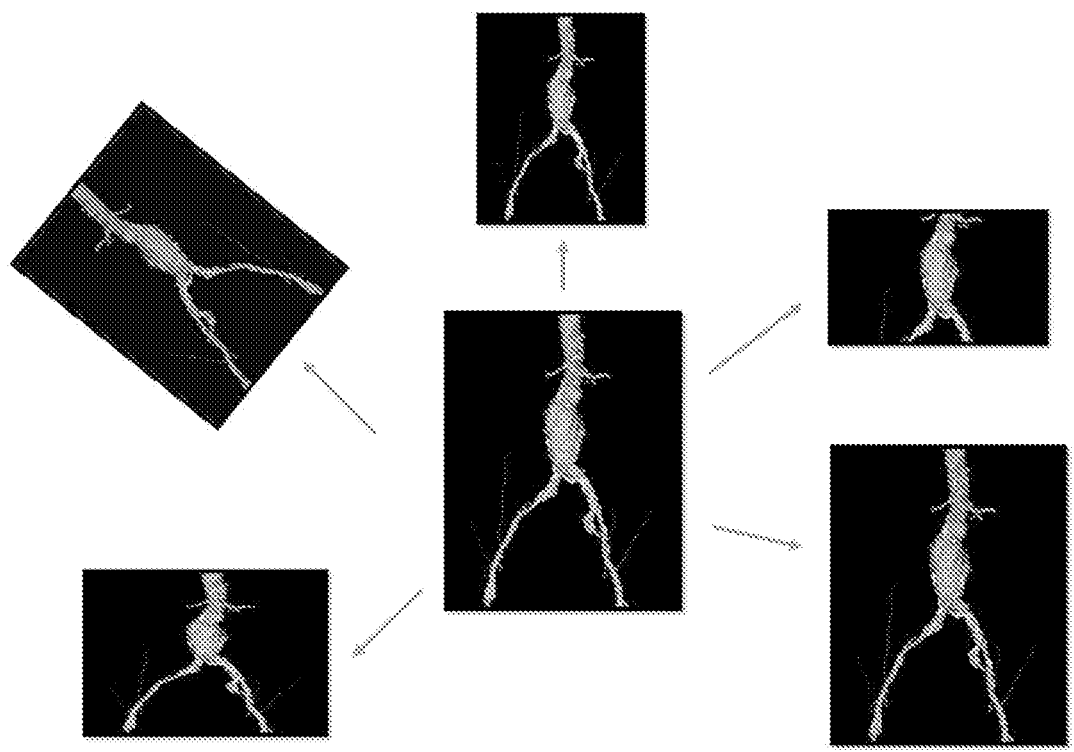
FIG. 4 illustrates examples of image augmentation, according to some embodiments.

FIG. 4 illustrates examples of image augmentation, according to some embodiments. The augmentation may include at least one of the following operations to the images: rotating, cropping, color jittering, blurring, and resizing. After the augmentation, the processed images may look visually similar to the original ones, but they are quite different in terms of representation and are considered new data to the model. The operations to the images may enlarge the dataset four-fold. Since data augmentation is applied simultaneously to both positive and negative cases, it did not reintroduce an imbalance issue.

The testing data may include pre-operative, intra-operative images, or post-operative 3D CTA images of patients diagnosed with AAA. The system provides the testing data to the prediction neural network 128 being trained with the training dataset. The prediction neural network 128 outputs a possibility that the patient may have post-operative complications if an endovascular aneurysm repair had been operated. The possibility of post-operative complications may be used to evaluate the risks of potential surgery.

Figure 5:
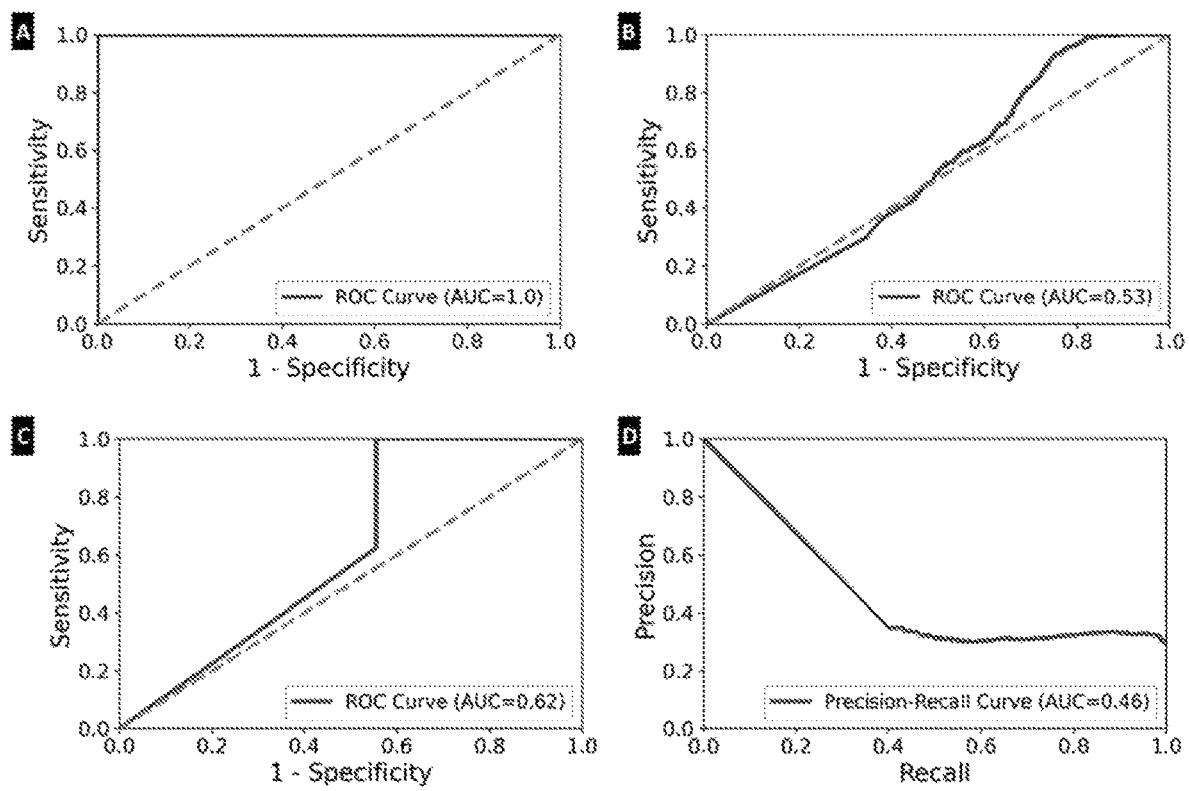
FIG. 5 shows examples of Receiver Operating Characteristic (ROC) curves and associated Area Under the Curve (AUC) scores for training the prediction neural network, according to some embodiments.

FIG. 5 shows examples of Receiver Operating Characteristic (ROC) curves and associated Area Under the Curve (AUC) scores for training the prediction neural network 128, according to some embodiments. ROC curve is a probability curve that plots the true positive rate against the false-positive rate at various threshold values. ROC curves have been used to evaluate classifier performance in machine learning. AUC is the sum of the ROC values and the AUC score is a measurement of the ability of a classifier to distinguish between classes. Usually, the higher the AUC, the better the performance of the neural network model at distinguishing between positive and negative classes.

FIG. 5A shows an example of a supposed to be "perfect model" that is able to perfectly distinguish between the positive and negative cases correctly. The ROC curve and AUC for the training data, with and without data augmentation, are both at 1.0. However, this model has overfitting during training. The model memorizes the details of each training case and afterward makes a false perfect training ROC curve. Additionally, due to the imbalance of data the model will always predict all the cases to be positive without data downsampling. Therefore, the ROC curve and AUC score in the testing, rather than the training, the dataset is a better reflection of how the model performs.

FIG. 5B shows a plot that has a ROC curve and an associated AUC score of 0.53 for the testing dataset, without data augmentation and using individual image prediction. Employing a majority vote can increase the AUC score to 0.57, while data augmentation with individual image prediction can improve the AUC score to 0.58. Combining both data augmentation and a majority vote can improve model performance and increase the AUC score to 0.62, as shown in FIG. 5C. FIG. 5D shows a precision-recall evaluation of prediction neural network 128, having an AUC score of 0.46.

As used herein, convolutional neural network, convolutional neural network model, prediction model, and AI model may be used interchangeably. In this specification, the term "module" is used broadly to refer to a software-based system, subsystem, or process that is programmed to perform one or more specific functions. Generally, a module will be implemented as one or more software modules or components installed on one or more computers in one or more locations. In some cases, one or more computers will be dedicated to a particular module; in other cases, multiple modules can be installed and running on the same computer or computers.

The following are non-limiting examples of embodiments of the disclosure herein.

In the example embodiment, a total of 501 patients who had an EVAR procedure have been studied. Of these, 273 patients meet inclusion criteria and are included in the training data. Patients who have undergone EVAR for ruptured abdominal aortic aneurysm (AAA), secondary EVAR after prior endovascular repair, or attempted EVAR and conversion to open repair may be excluded. The image data may be de-identified before being supplied to computing device 100.

In the example embodiment, a training:testing ratio of 5:1 may be used in one or more datasets so that the training data would have sufficient cases to test the performance of the neural network 128. According to the example embodiment, a positive:negative ratio in each dataset may be set to 1:4.7 to maintain the ratio of the whole training data. In other embodiments, different ratios for training:testing and positive:negative may be used.

In the example embodiment, the training data may be divided or classified according to a 1:4.7 positive:negative ratio into two sets depending on the development of post-operative complications.

In the example embodiment, a total of 40 positive and 189 negative cases may be randomly selected to form the training data to train the convolutional neural network model, while the remaining 8 positive and 36 negative cases later tested the performance of the model. The average age of the patients in the training data is 74±9 years with 221 (81%) of them being male (see Table 1). Hypertension and coronary artery disease are the most common comorbidities in this population, with 225 (82%) and 152 (56%) patients, respectively. A majority of patients have a current or former smoking history, with 172 (63%) being former smokers and 75 (28%) current smokers.

TABLE 1

| Demographic Data | | | |
|---|---|---|---|
| Age (years) | | 74 ± 9 | |
| Gender | Male | 221 | 81% |
| | Female | 52 | 19% |
| Comorbidities | HTN | 225 | 82% |
| | CAD | 152 | 56% |
| | DM | 66 | 24% |
| | Renal Failure | 54 | 20% |
| Smoking Status | Never Smoked | 26 | 10% |
| | Current Smokers | 75 | 28% |
| | Former Smokers | 172 | 63% |
| | Total Smokers | 247 | 91% |

The average initial AAA size prior to EVAR is 5.3+1.3 cm. Patients are followed for an average of 4 years after their procedure with five follow-up visits (see Table 2). Ultrasound scanning was used more frequently than CT.

TABLE 2

Follow-up Data

|  | Mean | Median | Range |
|---|---|---|---|
| AAA size (cm) | 5.6 ± 1.0 | 5.1 | 3.1-11.3 |
| Follow-up (years) | 3.8 ± 2.9 | 3.2 | 0-10 |
| Number of follow-up visits | 5.2 ± 3.2 | 5.0 | 0-16 |
| Type of follow-up |  |  |  |
| Ultrasound | 3.0 ± 2.5 | 3.0 | 0-11 |
| CT | 0.4 ± 1.0 | 0 | 0-7 |
| Office visit | 1.6 ± 1.3 | 1 | 0-7 |
| Other | 0.2 ± 0.7 | 0 | 0-6 |

A total of 48 (17.6%) patients have one or more complications after EVAR (see Table 3). This included 4 ruptures (1.5%) and 40 (14.7) endoleaks of which type II is most commonly seen in 32 out of the 40 patients. One patient had both a type III and type IV endoleak while another patient had type I and type II endoleak. No patients have pelvic ischemia or graft fatigue. Of the patients who have developed complications after EVAR, 7 (14.6%) required reintervention.

TABLE 3

Complications

| Complication Type | Number | Percentage of Total (N = 273) | Percentage of Complications (N = 48) |
|---|---|---|---|
| Total Complications | 48 | 17.6% | 100% |
| Limb Occlusion | 7 | 2.6% | 14.6% |
| AAA Rupture | 4 | 1.5% | 8.3% |
| Graft Infection | 2 | 0.7% | 4.2% |
| Graft Migration | 1 | 0.4% | 2.1% |
| Renal Artery Occlusion | 1 | 0.4% | 2.1% |
| Neck Dilation | 1 | 0.4% | 2.1% |
| Endoleak | 40 | 14.7% | 83.3% |
| Type I | 5 | 1.8% | 10.% |
| Type II | 32 | 11.7% | 66.7% |
| Type III | 3 | 1.1% | 6.3% |
| Type IV | 1 | 0.4% | 2.1% |
| Unspecified | 1 | 0.4% | 2.1% |

After the prediction model is established, the test data may include one or more cases that have never been exposed to the prediction model. In the example embodiment, 44 cases of pre-operative 3D CTA reconstruction images are used. The prediction model correctly identifies all 8 patients who subsequently had complications. Of the 36 negative cases, 20 are correctly predicted as negative, while 16 are incorrectly predicted to be positive and have complications. The sensitivity, specificity and negative predictive values for this model are 100%, 44%, and 100%, respectively (see Table 4).

TABLE 4

Prediction Results

|  | Complication (Actual) | No Complication (Actual) |
|---|---|---|
| Positive (Predicted) | 8 | 20 |
| Negative (Predicted) | 0 | 16 |

The invention claimed is:

1. A computer-implemented method for predicting post-operative complications after endovascular aneurysm repair, the method comprising:
    calculating a post-operative complication probability of a patient after endovascular aneurysm repair, wherein calculating the post-operative complication probability comprises:
        generating a plurality of 3-dimensional computed tomography angiography (3D CTA) reconstruction images of the patient; and
        providing the plurality of 3D CTA reconstruction images of the patient to a prediction neural network configured to predict post-operative complications after endovascular aneurysm repair, wherein the prediction neural network is trained on a set of training data comprising a plurality of training examples, and wherein training the prediction neural network comprises:
    generating one or more datasets including a plurality of post-operative 3D CTA reconstruction images of patients after endovascular aneurysm repair;
    selecting a first set of images showing positive post-operative complications and a second set of images showing negative post-operative complications in accordance with a determined positive:negative ratio;
    generating a set of downsampled images by downsampling the second set of images using a downsampling ratio of n;
    generating augmented images by augmenting the first set of images and the set of downsampled images;
    determining a training put from the augmented images; and
    providing the training input to the prediction neural network.

2. The method of claim 1, wherein the 3D CTA reconstruction images are at least one of pre-operative, intra-operative, and post-operative images.

3. The method of claim 1, wherein the determined positive:negative ratio is 1:4.7.

4. The method of claim 1, wherein augmenting the downsampled first set of images and the downsampled second set of images includes rotating, cropping, color jittering, blurring and resizing the plurality of 3D CTA reconstruction images.

5. The method of claim 1, wherein the post-operative complications include at least one of endoleak, graft migration, abdominal aortic aneurysm rupture, graft limb occlusion, renal artery occlusion, neck dilation, graft infection, pelvic ischemia, and barb fracture.

6. The method of claim 1, wherein the downsampling ratio of n is 4.7.

7. The method of claim 1, wherein the one or more datasets include clinical demographic characteristics.

8. The method of claim 1, wherein the one or more datasets include comorbidities.

9. A computer system for predicting post-operative complications after endovascular aneurysm repair, comprising:
    one or more non-transitory digital storage media storing computer-executable instructions; and
    one or more processors couple to the one or more non-transitory digital storage media and configured to execute the computer-executable instructions to calculate a post-operative complication probability of a patient after endovascular aneurysm repair, wherein calculating the post-operative complication probability comprises:
  generating a plurality of 3-dimensional computed tomography angiography (3D CTA) reconstruction images of the patient; and
  providing the plurality of 3D CTA reconstruction images of the patient to a prediction neural network configured to predict post-operative complications after endovascular aneurysm repair, wherein the prediction neural network is trained on a set of training data comprising a plurality of training examples, and wherein training the prediction neural network comprises:
    generating one or more datasets including a plurality of post-operative 3D CTA reconstruction images of patients after endovascular aneurysm repair;
    selecting a first set of images showing positive post-operative complications and a second set of images showing negative post-operative complications in accordance with a determined positive:negative ratio;
    generating a set of downsampled images by downsampling the second set of images using a downsampling ratio of n;
    generating augmented images by augmenting the first set of images and the set of downsampled images;
    determining a training put from the augmented images; and
    providing the training input to the prediction neural network.

10. The computer system of claim 9, wherein the 3D CTA reconstruction images are at least one of pre-operative, intra-operative, and post-operative images.

11. The computer system of claim 9, wherein the determined positive:negative ratio is 1:4.7.

12. The computer system of claim 9, wherein augmenting the downsampled first set of images and the downsampled second set of images includes rotating, cropping, color jittering, blurring and resizing the plurality of 3D CTA reconstruction images.

13. The computer system of claim 9, wherein the post-operative complications include at least one of endoleak, graft migration, abdominal aortic aneurysm rupture, graft limb occlusion, renal artery occlusion, neck dilation, graft infection, pelvic ischemia, and barb fracture.

14. The computer system of claim 9, wherein the one or more datasets include clinical demographic characteristics and comorbidities.

15. One or more non-transitory digital storage media storing one or more sequences of program instructions which, when executed using one or more processors, cause the one or more processors to calculate a post-operative complication probability of a patient after endovascular aneurysm repair, wherein calculating the post-operative complication probability comprises:
  generating a plurality of 3-dimensional computed tomography angiography (3D CTA) reconstruction images of the patient; and
  providing the plurality of 3D CTA reconstruction images of the patient to a prediction neural network configured to predict post-operative complications after endovascular aneurysm repair, wherein the prediction neural network is trained on a set of training data comprising a plurality of training examples, and wherein training the prediction neural network comprises:
    generating one or more datasets including a plurality of post-operative 3D CTA reconstruction images of patients after endovascular aneurysm repair;
    selecting a first set of images showing positive post-operative complications and a second set of images showing negative post-operative complications in accordance with a determined positive:negative ratio;
    generating a set of downsampled images by downsampling the second set of images using a downsampling ratio of n;
    generating augmented images by augmenting the first set of images and the set of downsampled images;
    determining a training put from the augmented images; and
    providing the training input to the prediction neural network.

16. The one or more non-transitory digital storage media of claim 15, wherein the 3D CTA reconstruction images are at least one of pre-operative, intra-operative, and post-operative images.

17. The one or more non-transitory digital storage media of claim 15, wherein the determined positive:negative ratio is 1:4.7.

18. The one or more non-transitory digital storage media of claim 15, wherein augmenting the downsampled first set of images and the downsampled second set of images includes rotating, cropping, color jittering, blurring and resizing the plurality of 3D CTA reconstruction images.

19. The one or more non-transitory digital storage media of claim 15, wherein the post-operative complications include at least one of endoleak, graft migration, abdominal aortic aneurysm rupture, graft limb occlusion, renal artery occlusion, neck dilation, graft infection, pelvic ischemia, and barb fracture.

20. The one or more non-transitory digital storage media of claim 15, wherein the one or more datasets include clinical demographic characteristics and comorbidities.

* * * * *